(12) United States Patent  
Schoellhorn (10) Patent No.: US 7,507,202 B2  
(45) Date of Patent: Mar. 24, 2009

(54) RETRACTOR FOR PERFORMING HEART AND THORAX SURGERIES

(75) Inventor: Joachim Schoellhorn, Freiburg (DE)

(73) Assignee: Karl Storz GmbH & Co. KG (DE)

( * ) Notice: Subject to any disclaimer, the term of this patent is extended or adjusted under 35 U.S.C. 154(b) by 328 days.

(21) Appl. No.: 11/287,717

(22) Filed: Nov. 28, 2005

(65) Prior Publication Data

US 2006/0089537 A1 Apr. 27, 2006

Related U.S. Application Data

(63) Continuation of application No. PCT/EP2004/005468, filed on May 21, 2004.

(30) Foreign Application Priority Data

May 28, 2003 (DE) ................................ 103 25 393

(51) Int. Cl.
*A61B 17/02* (2006.01)
(52) U.S. Cl. ........................................... 600/232
(58) Field of Classification Search ......... 600/231–233, 600/210, 213, 222
See application file for complete search history.

(56) References Cited

U.S. PATENT DOCUMENTS

| 5,025,779 | A | 6/1991 | Bugge | 128/20 |
|---|---|---|---|---|
| 5,931,778 | A * | 8/1999 | Furnish | 600/232 |
| 5,967,972 | A | 10/1999 | Santilli et al. | 600/232 |
| 6,099,468 | A * | 8/2000 | Santilli et al. | 600/232 |
| 6,159,231 | A | 12/2000 | Looney et al. | 606/206 |
| 6,416,468 | B2 | 7/2002 | Deckman et al. | 600/231 |
| 6,478,734 | B1 | 11/2002 | Taylor et al. | 600/217 |
| 6,569,091 | B2 * | 5/2003 | Diokno et al. | 600/220 |

FOREIGN PATENT DOCUMENTS

| DE | 198 57 320 | 6/2000 |
|---|---|---|
| DE | 200 03 335 | 7/2000 |

OTHER PUBLICATIONS

PCT International Search Report, Aug. 24, 2004, 3 pages.
English translation of the International Preliminary Report on Patentability, Apr. 27, 2006, 6 pages.

* cited by examiner

*Primary Examiner*—Ralph A Lewis
(74) *Attorney, Agent, or Firm*—St. Onge Steward Johnston & Reens LLC (57) ABSTRACT

A retractor has a rail, a first holding arm protruding from this rail at an angle at a second holding arm extending approximately parallel to the first holding arm. A distance between the two arms being modifiable. At least one functional element is mounted on one of these holding arms, which functional element has a section extending transversely to the holding arms and a swivel bracket protruding from this transverse section. The functional element being pivotable about a pin extending roughly parallel to the arms via the swivel bracket, a swiveled position can be set by grasping the function element with a hand. A locking mechanism serves for locking the functional element in a swiveled position.

13 Claims, 6 Drawing Sheets

RETRACTOR FOR PERFORMING HEART AND THORAX SURGERIES

CROSSREFERENCE OF PENDING APPLICATION

This application is a continuation of pending international application PCT/EP2004/005468 filed on May 21, 2004 which designates US and which claims priority of German patent application 103 25 393.9 filed on May 28, 2003.

BACKGROUND OF THE INVENTION

The invention concerns a retractor with a rail from which a first holding arm protrudes at an angle and with a second holding arm which extends approximately parallel to the first holding arm and the distance from which is modifiable, and with functional elements mounted on the holding arms, of which at least one functional element has a section that extends transversely to a holding arm and which can be pivoted around a pin roughly parallel to one holding arm.

A retractor of this kind is, for example, known from document U.S. Pat. No. 5,025,779 or from U.S. Pat. No. 6,478,734 B1.

Retractors of this kind are for example used as rib retractors in open-heart surgery. The specialist terms thoracic and sternal retractors have become established here.

When a retractor is used on the sternum, the sternum (breastbone) is divided longitudinally and the functional elements attached to each of the holding arms are inserted into the opening in the sternum. Activating the drive mechanism moves the two holding arms apart and the thorax is opened up, enabling the surgeon to perform surgery inside the chest cavity.

Sternal retractors are used mainly in surgeries in which coronary vessels are replaced by other vessels; these are known as bypass surgeries. The left internal thoracic artery is currently generally used for this purpose. Technically, this is usually referred to as the (left) internal mammary artery, or (L)IMA for short. For this reasons, retractors used for this type of operation are also called IMA or LIMA retractors.

A further refinement of this surgery method is known as the minimally invasive direct coronary artery bypass (MIDCAB) technique. It was developed in the context of minimally invasive surgery. Here, access to the heart is gained not by opening the breastbone but via one of the intercostal spaces. The instruments developed for this purpose are known technically as MIDCAB retractors or sometimes also as lateral retractors.

It has proved useful for both techniques if the retractors used not only pull the two sides of the thorax opening apart but also raise the half of the thorax on the heart side in relation to the other one, since this gives better access to the heart.

U.S. Pat. No. 5,025,779 describes a rib retractor for raising one side of the thorax opening in relation to the other. The device described in the document has at least one functional element which is pivotable around a pin parallel to a holding arm, and the swivel position of which in relation to the retractor rail can be altered by means of an adjusting device.

This adjusting device is an adjusting screw. It passes through a swivel bracket by means of which the functional element is fixed to the holding arm, and rests against the section of the functional element which is at right angles to the holding arm. Turning the adjusting screw alters the distance between the swivel bracket and the functional element at the level of the adjusting screw. The fact that the swivel bracket and the functional element are connected such that they can pivot at a second place produces the desired change in the swivel position.

Use of a positioning device of this kind does have its disadvantages, however. One disadvantage of such a design is that the surgeon cannot feel exactly how much force is being applied to the patient's body, since the change in the swivel position is, as described above, made by turning an adjusting screw.

The amount of force applied to the patient's body acts along the axis of the positioning device. The force is absorbed partly by the positioning device and partly by the connection between the swivel bracket and the functional element. The only feeling which the surgeon has of the force applied is the degree of resistance encountered by the adjusting screw. The application of too much force may lead to trauma in the operating site.

A positioning device of this kind also places a relatively high focal stress on the functional element. Retraction of the thorax requires a high level of force, because the thorax is made up of numerous bones, muscles and tendons.

This high level of force thus acts directly on the relatively small bearing surface of the adjusting device.

Also, raising one half of the chest by means of an adjusting screw is time-consuming. To guarantee both sufficient accuracy of adjustment and an easy passage for the adjusting screw, adjusting screws with a narrow thread and small pitch are used. This means that the change in the swivel position per turn of the screw is small, thus necessitating prolonged screwing when there is a large change in the swivel position.

U.S. Pat. No. 6,159,231 describes a retractor in which the rail on which the two holding arms are mounted is angled. Here, raising the retractor is done using another external mechanism, such as a cable device.

This device does however have the disadvantage that it markedly reduces the surgeon's access to the operating site. With this design, the operating site can be accessed only from the side away from the lifting mechanism. Also, the device described in the patent is not symmetrical, and can therefore be used only for one side of the chest, generally the left one.

DE-C-198 57 320 describes a rib retractor in which the rail on which the two holding arms are mounted is in the shape of a convex arch. The retractor described has no other elements for raising one side of the operating window in relation to the other. This means that the difference in height between the two sides of the operating window is directly dependent on the width of the opening. This is determined solely by the fixed curvature of the arch-shaped rail. This means that the retractor cannot be adjusted to accommodate the circumstances of a particular operation.

U.S. Pat. No. 6,416,468 describes a lateral rib retractor which has a foot attached to one of the two holding arms. The device described in this patent is mechanically complicated and consists of a large number of individual parts, which makes it costly to manufacture and complicated to clean and sterilize. Also, the use of a separate foot can resulting in the foot slipping off and disrupting the operation.

U.S. Pat. No. 6,478,734 B1 describes as a fifteenth embodiment a retractor having a blade arm which is rotatably coupled via a cylindrical shaft to a drive block. The axis of the shafts extends into a longitudinal extension of the drive block. The blade arm is connected to a pad arm provided with a ratchet mechanism for turning blade arm via pad arm about the cylindrical shaft and locking said blade arm in different turning positions. This bulky blade arm/pad arm construction does not enable a surgeon to directly lift the chest but only via a lever. The lever geometry of blade arm/pad arm allows a simultaneous spreading and lifting movement only.

It is therefore the object of the invention to create a retractor for raising the ribs whereby the raising of one half of the chest is atraumatic and can be performed manually by the surgeon who can feel what he is doing.

SUMMARY OF THE INVENTION

This object can be achieved in that the swivel position of the functional element can be set grasping it with the hand and lifting it, and fixed using a locking mechanism.

Since the swivel position is set by raising the device manually, the surgeon can at any time feel how much force is being applied to the patient's chest, and can thus avoid injury caused by overloading. Once the swivel position required by the surgeon has been reached, it is fixed by means of the locking mechanism.

The locking mechanism has the advantage that it is of a simple mechanical design. It can for example be a click system, a system fastened by means of pins, or another design known in the art.

In a preferred embodiment, the locking mechanism takes the form of a click mechanism.

A click mechanism is a particularly advantageous locking mechanism, since it makes setting the swivel position particularly simple and sensitive; use of a click mechanism can also avoid any slippage when the swivel position is being set.

The swivel position can be fixed using the click mechanism with just one hand. One useful point is that the catch can move in the direction in which the one half of the chest is to be lifted, and locks in the direction in which that half of the chest would be lowered. This means that the half of the chest can be brought into the desired position simply by raising it with one hand, then locked into the desired position by briefly lowering it again.

In one preferred embodiment of the abovementioned device, the click mechanism consists of a rack and a locking catch.

A click mechanism of this kind is remarkable for its particular mechanical simplicity, since it can be made from very few components and has no other moving parts, which considerably simplifies both the manufacture of the retractor and its cleaning and sterilization.

In another preferred embodiment of the abovementioned device, the locking catch is formed by a notch in the functional element.

The fact that the locking catch is formed by a notch in the functional element greatly simplifies manufacture of the functional element. This also avoids corners and recesses in which bacteria can become lodged and which are difficult to clean and sterilize.

In another preferred embodiment, the locking catch is bevelled on the side facing the rack.

This feature ensures the locking catch engages particularly firmly with the rack.

In another preferred embodiment, the rack points away from the retractor roughly at a right angle to the longitudinal axis of the holding arm.

Having the rack pointing in this direction means that it is pointing away from the surgery site and avoids any hindrance of the surgeon. It also minimizes the risk of any unwanted movement of the rack.

In another preferred embodiment, the locking mechanism has a T-shaped handle.

The use of a T-shaped handle makes it much easier to operate the locking mechanism. A T-shaped handle also facilitates one-handed fixing of the swivel position, since if the functional element is grasped with the hand, the handle can be operated with the thumb.

In another preferred embodiment, the functional element can be moved freely on the holding arm.

The free mobility of the functional element means that the retractor can be adapted to the anatomy of the particular patient.

In another preferred embodiment of the abovementioned design, the functional element can be removed from the holding arm.

The fact that the functional element can be removed from the holding arm makes it much easier to clean and sterilize the retractor.

In another preferred embodiment of the abovementioned design, the functional element can be attached to any of the holding arms.

This feature considerably increases the flexibility of the retractor. This means that the retractor can be used in surgery on both the left-and the right-hand side of the chest, as both a lateral retractor and as a sternal retractor. It also gives the surgeon much more freedom in choosing how the retractor lies on the patient.

In another preferred embodiment, the functional element has at least partially a contoured surface on the areas where it is at the edge of a operating window or in the body.

This feature has the advantage that the structured surface promotes fixation between the functional element and the body tissue. This means that the retractor can be handled without this affecting the firm grip of the functional element on the tissue.

In another preferred embodiment of the abovementioned design, the surface structure has a crossed herringbone pattern.

This feature has the advantage that it can not only be manufactured well but also that it allows immobile and atraumatic attachment to the tissue in a variety of spatial planes.

In another preferred embodiment, the surface structure has pyramid-shaped elevations with a rhombus-shaped base.

This feature has the advantage that the rhombus structure of the surface patterning allows differing resistances to slippage to be created in two different spatial planes perpendicular to one another. Thus, slippage in the direction of the longer diagonal of the rhombus is more likely than in the direction of the shorter diagonal of the rhombus, since the elevations offering resistance are much broader in this direction. There are also far more elevations per unit of length in this direction.

Advantageously, the functional element is mounted on one holding arm and a valve is mounted on the other.

In this design the retractor is particularly well suited to the performance of cardiothoracic surgical procedures.

Obviously, the features mentioned above and those that have still to be explained below can be used not only in the combination mentioned in each case but also in other combinations or even alone, without going beyond the scope of the present invention.

BRIEF DESCRIPTION OF THE DRAWINGS

Exemplary embodiments of the invention are shown in the drawing and are described in more detail below. The figures show.

DETAILED DESCRIPTION OF PREFERRED EMBODIMENT

Figure 1:
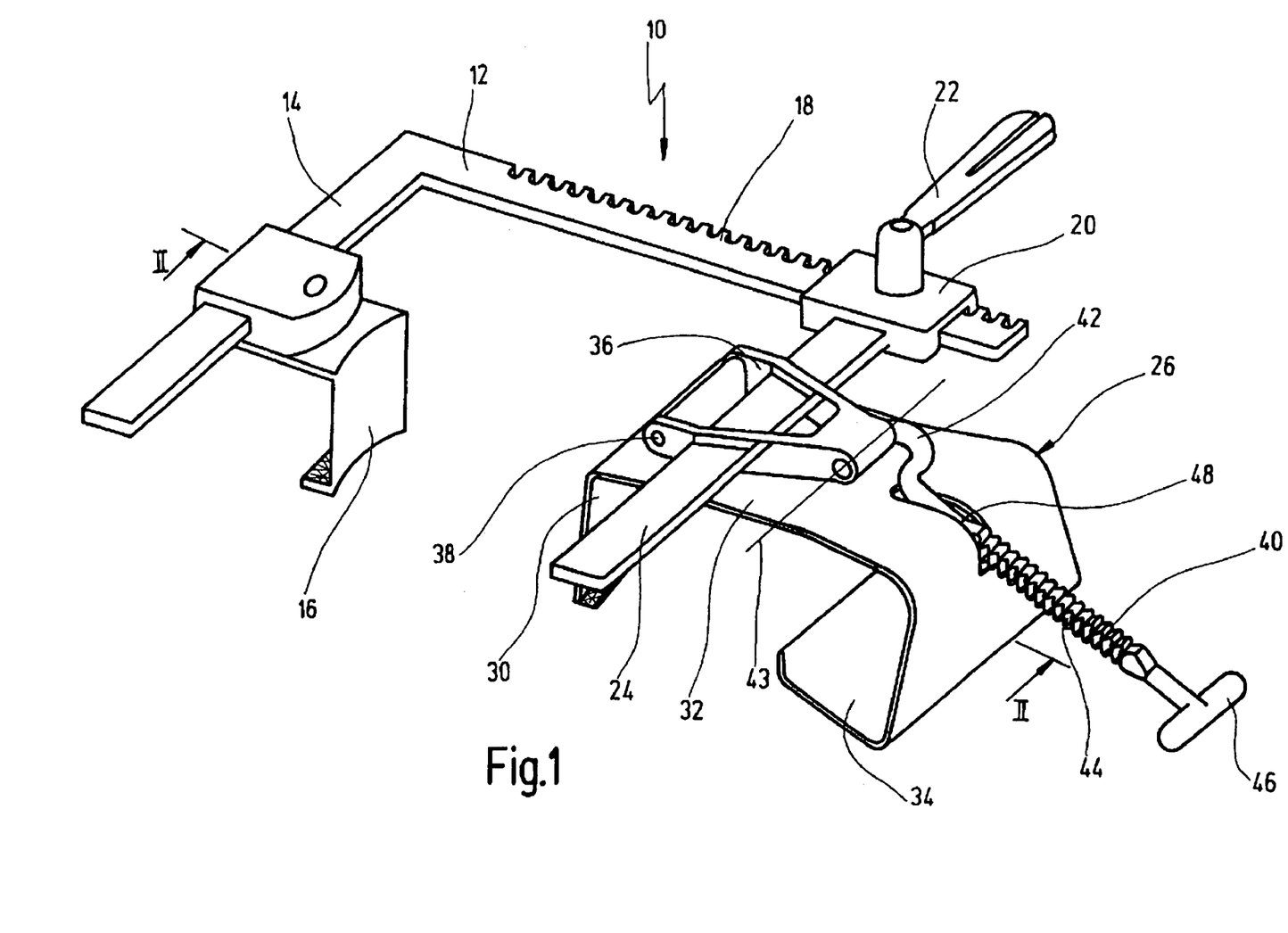
FIG. 1 a perspective view of a retractor in accordance with the invention, with a functional element in accordance with the invention, FIG. 2 a perspective view of a functional element in accordance with the invention, removed from the retractor, swivelled upwards, FIG. 3 a section through a functional element in accordance with the invention, along line IV-IV of FIG. 2, FIG. 4 an enlargement of the circled section of FIG. 3, FIG. 5 a cross section of a human thorax in which a retractor is being used, FIG. 6 a view of the opened retractor corresponding to the sectional diagram in FIG. 5, and FIG. 7 a view corresponding to FIGS. 5 and 6, with half of the chest raised, shortly before fixation by means of the locking mechanism.

FIG. 1 shows a retractor in accordance with the invention, in its entirety and marked with the reference numeral 10.

The retractor 10 has a rail 12 on which a holding arm 14 is mounted at right angles. This holding arm 14 has a valve 16 movably mounted on it.

The rail 12 also has a rack section 18 on which a drive mechanism 20 is movably mounted. The drive mechanism 20 is moved by means of a cogwheel, not shown in the drawing, which engages with the teeth of the rack section 18. This cogwheel is operated by means of a handle 22.

Also mounted on drive mechanism 20 is a second holding arm 24 which is roughly at right angles to the rail 12. A functional element 26 is movably mounted on this holding arm 24.

The functional element 26 (see also FIGS. 2 and 3) has a valve section 30 which is roughly parallel to the valve 16, a transverse section 32 which is at right angles to the holding arm 24, and a supporting section 34. The transverse section 32 is pivotably connected to a swivel bracket 36. The swivel bracket 36 has for this purpose, at one end, a kingpin 38 to which functional element 26 is attached.

There is also a correspondingly shaped hook 56 (see FIG. 3) standing upright on the upper side of transverse section 32 for this purpose.

The swivel bracket 36 has two openings 52 and 54 (see in particular FIG. 2) through which a holding arm 24 can be pushed (see in particular FIG. 1). This allows the functional element 26 to be fitted to retractor 10 so that it can be moved along it.

Figure 2:
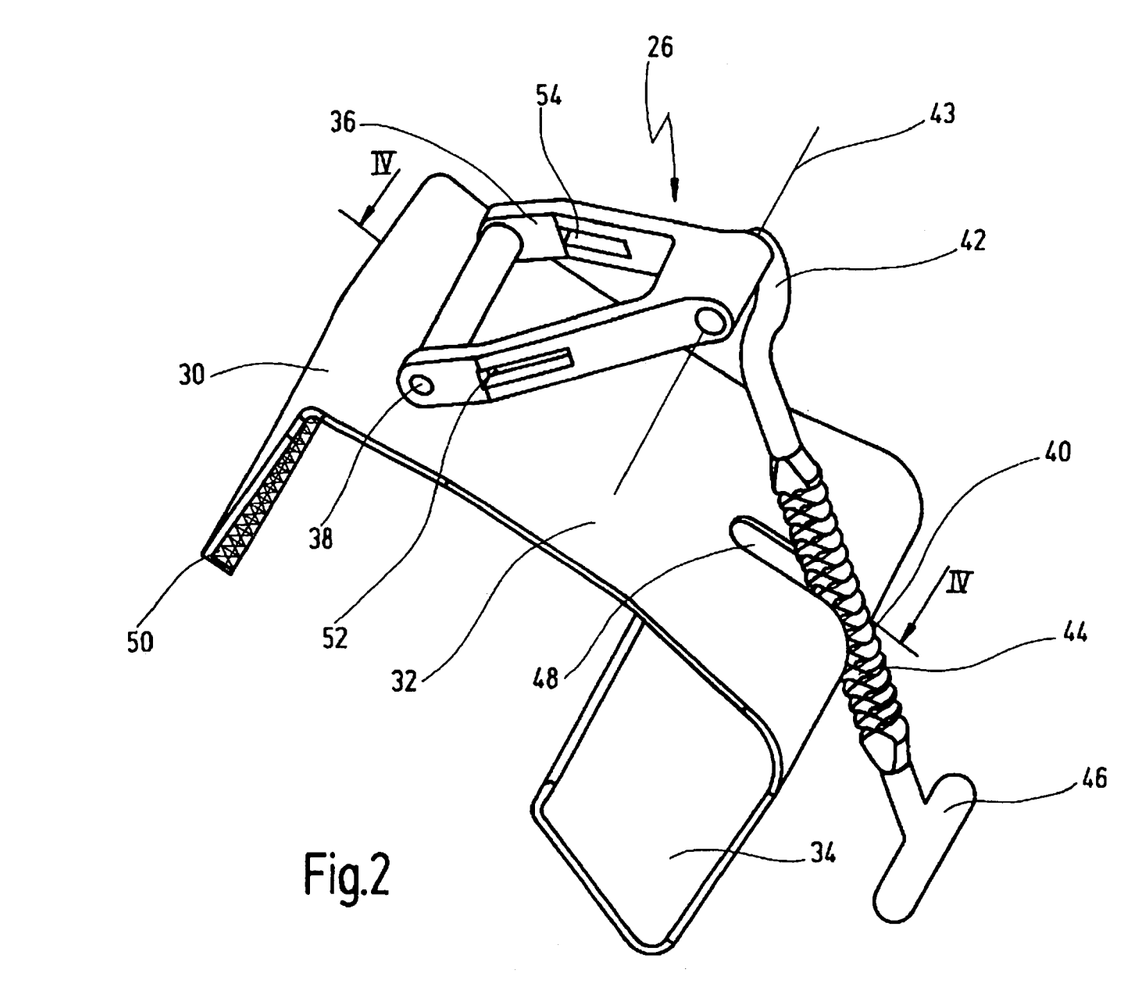

The swivel bracket 36 is, at the end opposite the kingpin 38, connected to an adjusting device 40. This adjusting device has a U-shaped, hooked section 42 which is connected to the swivel bracket 36. The terminal section of the U-shaped section 42 is inserted sideways into an opening in the swivel bracket 36 and can be pivoted around a pin 43 which runs roughly parallel to the holding arm 14. The adjusting device 40 is thus pivotably connected to the swivel bracket 36.

The adjusting device 40 also has a rack 44 which runs more or less at right angles to the holding arm 24 and thus points away from the retractor 10. A T-shaped handle 46 is mounted at the end of the rack 44.

In this view, the rack 44 engages with a notch 48 in the functional element 26. This notch 48 is slit-shaped and runs, in the transitional region, from transverse section 32 to supporting section 34.

FIG. 2 shows a functional element 26 removed from the retractor 10; transverse section 32 and swivel bracket 36 are pivoted in relation to one another.

In this view it can be seen that the valve section 30 of the functional element 26 has a rhombus-shaped pattern 50 on its inside.

In this view, the transverse section 32 opposite the swivel bracket 36 was pivoted around the kingpin 38. The hooked section 42 of the adjusting device 40 was raised here in relation to the transverse section 32. The adjusting device 40 was pivoted around the axis 43 in relation to the swivel bracket 36; the rack 40 in turn comes to rest in the notch 48.

Figure 3:
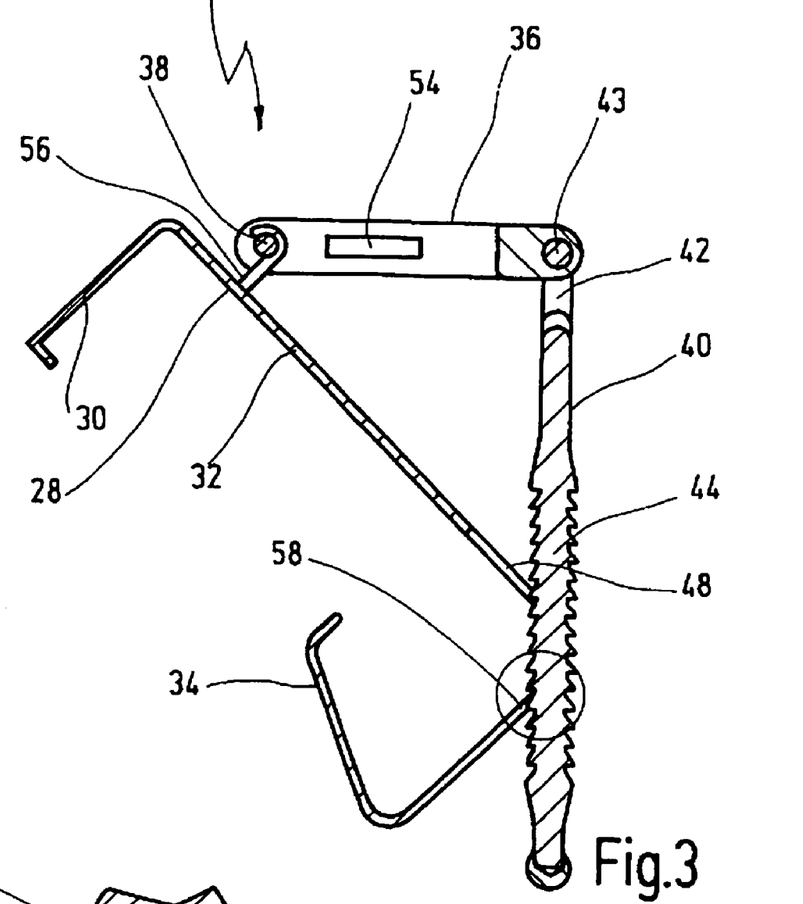

In FIG. 3 the hook 56 mounted on the transverse section 32 is visible.

It can also be seen that the bottom edge of the notch 48 forms a locking catch 58 in the region of the supporting section 34 of the functional element 26; here it rests on the rack 44.

Figure 4:
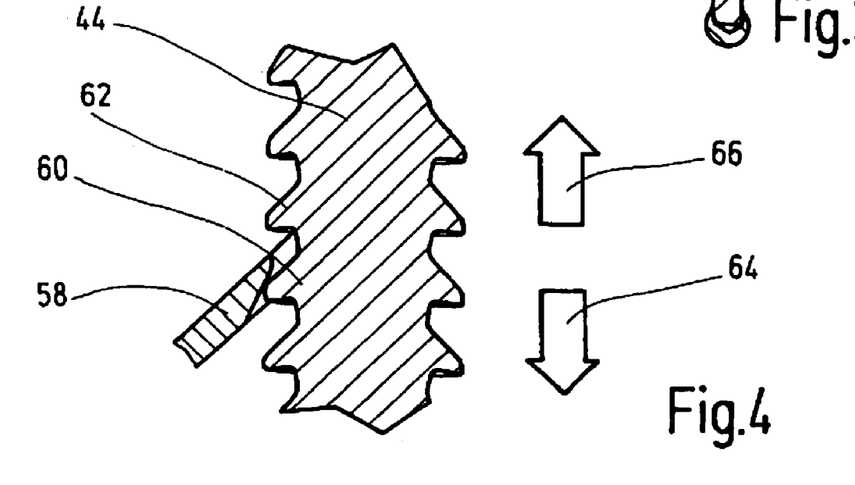

FIG. 4 shows an enlarged section of FIG. 3 which shows how the locking catch 58 rests on a tooth 60 of the rack 44. It is also visible here that the locking catch 58 is bevelled. The beveling is touching an oblique edge of the tooth 60.

This Figure shows that the locking catch 58 moves in the direction of arrow 64 and can slide past the tooth 60 and can thus move freely in this direction. In a movement the other way, in the direction of arrow 66, the locking catch strikes the edge of the tooth 62 which is at right angles to the longitudinal axis of the rack 44, as a result of which movement in the direction of arrow 66 is blocked.

Figure 5:
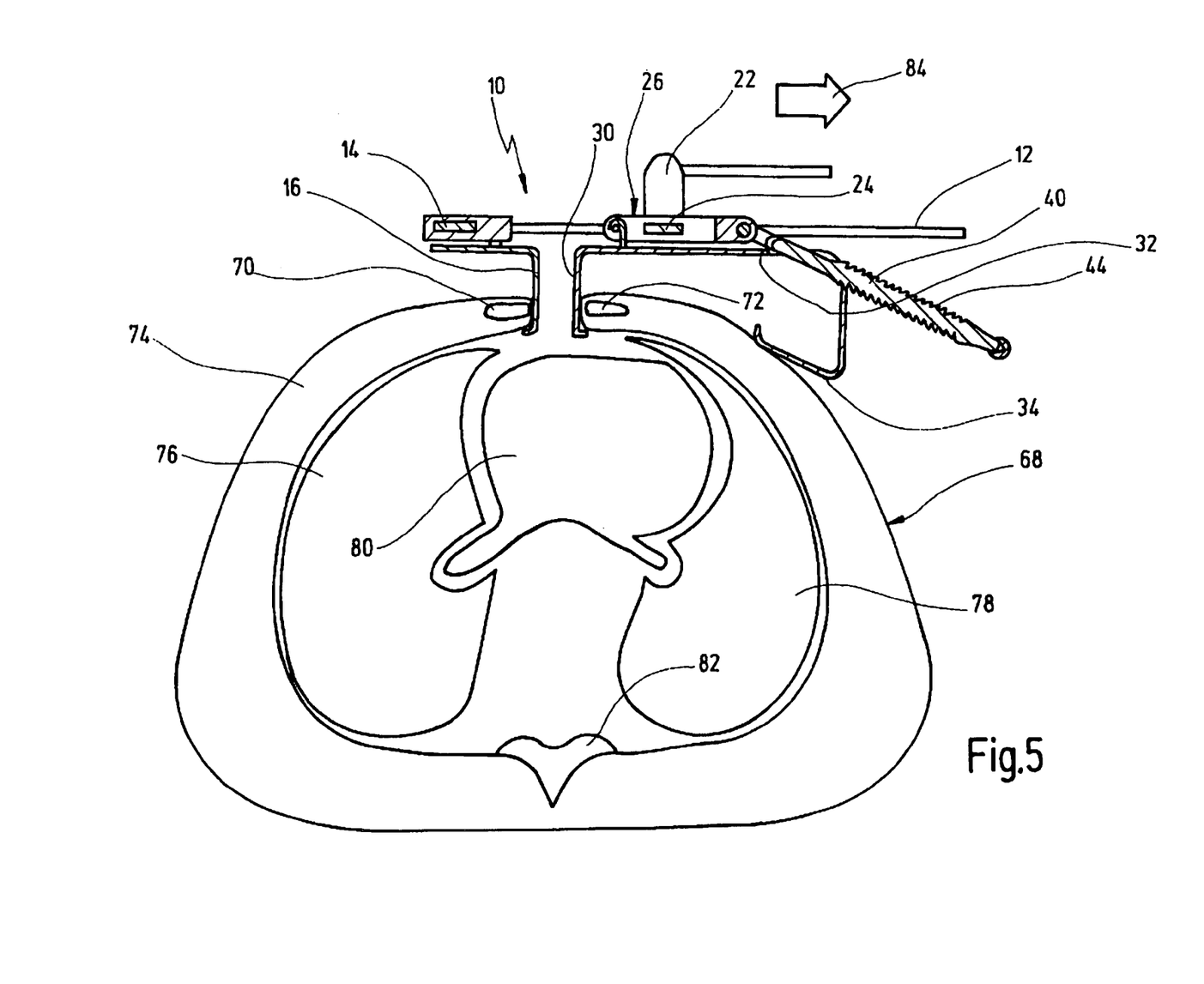

FIG. 5 is a schematic view of a section through a body 68 of a patient, with a retractor 10 in accordance with the invention inserted into the surgery site. An opening was created by dividing the breastbone into the two parts 70 and 72. The two halves of the breastbone form part of the thorax 74. Inside the thorax 74, the two pulmonary lobes 76 and 78 and the heart 80 can be seen. A thoracic vertebra 82 can be seen in the lower region of the thorax 74.

In this view, the retractor 10 is still in the closed position. Turning the handle 22 moves the holding arm 24 along the rail 12 in the direction of arrow 84 away from holding arm 14. This moves the functional element 26 away from the valve 16 in the direction of arrow 84 and the opening in the breast in the patient's thorax 74 is extended.

Figure 6:
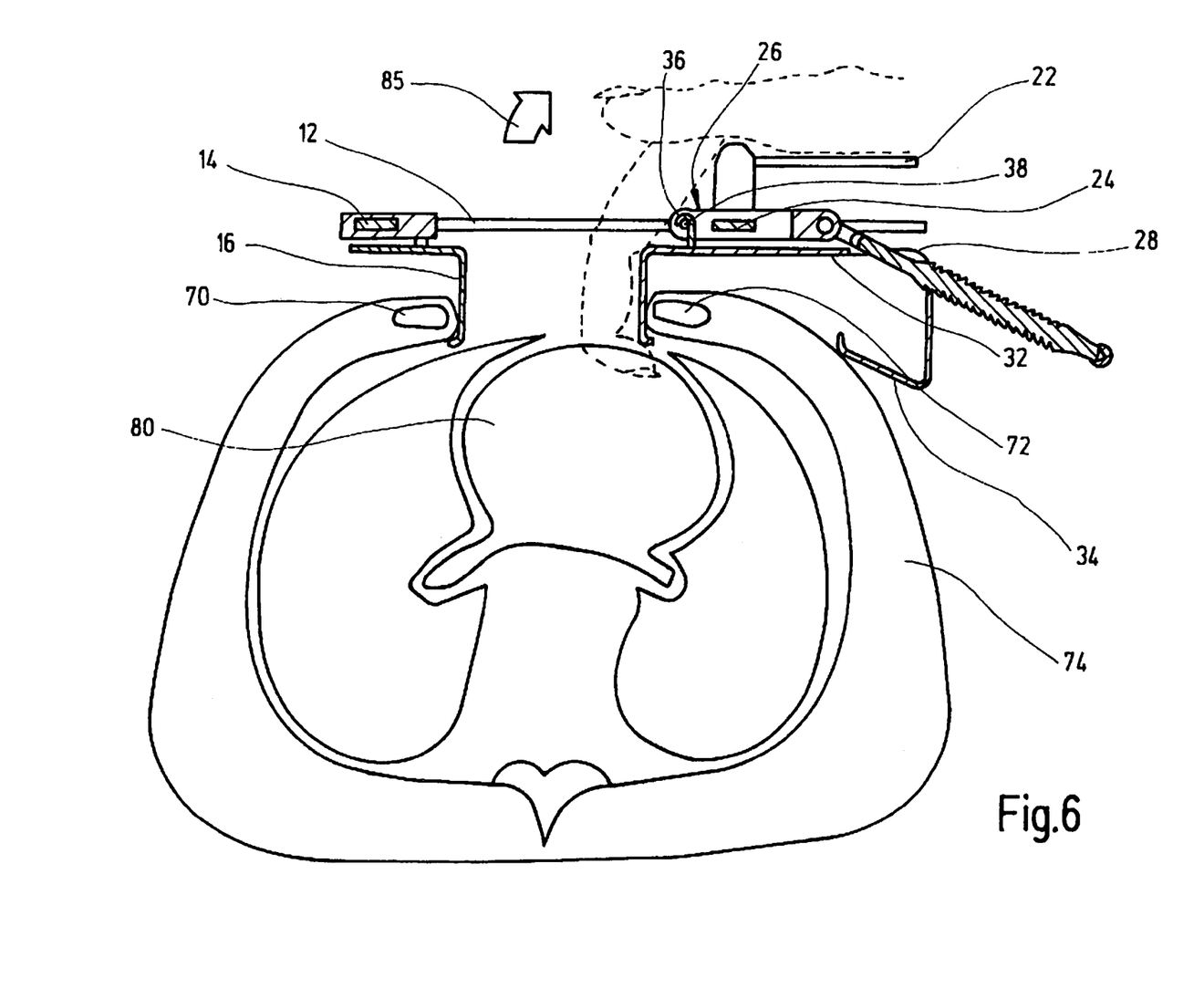

FIG. 6 shows a view similar to that of FIG. 5, whereby turning the handle 22, as previously described, moves the holding arm 24 away from the holding arm 14 and thus moves the functional element 26 away from the valve 16. This makes it clear that access to the heart 80 is already much somewhat easier. The dotted lines show the surgeon's hand reaching into the opening in the breast in order to raise the functional element 26 in the direction of arrow 85. In so doing the swivel bracket 36 is raised and the functional element 26 is pivoted out in relation to the swivel bracket 36. The supporting section 34 of the functional element 26 remains in constant contact with the outside of the thorax 74. During the lifting process, the locking catch 58 runs over the bevelled edges of the teeth 60 and 62.

Figure 7:
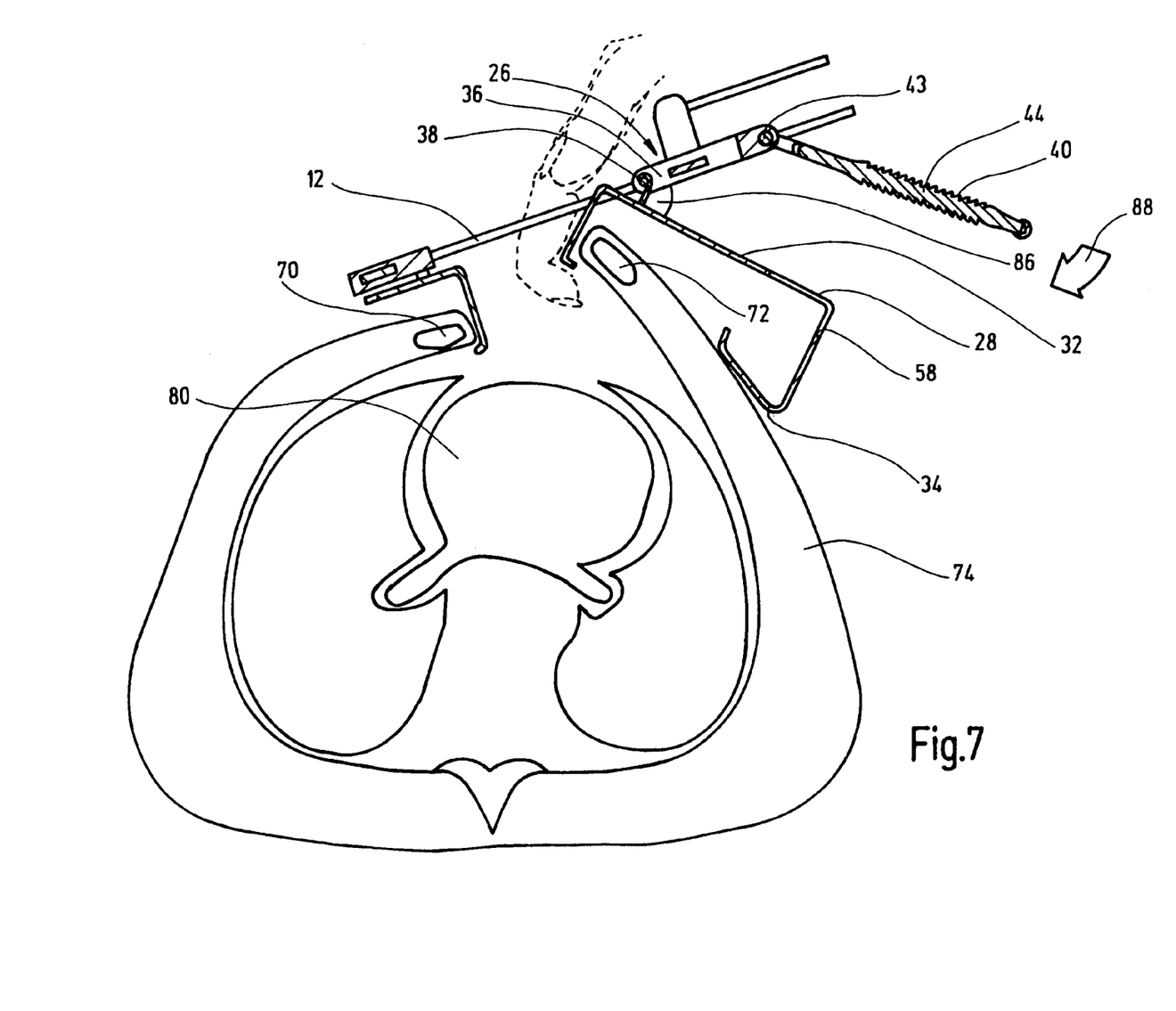

FIG. 7 shows a section similar to that in FIG. 6, in which the functional element 26 has been raised by the hand indicated by the dotted line. Here the transverse section 32 is pivoted through the angle 86 in relation to the swivel bracket 36. This pivoting occurs around the kingpin 38. It can also be seen that the right half of the breastbone 72 is clearly raised in comparison to the left half of the breastbone 70 and that access to the heart 80 has been markedly improved. When moving the rack 44 along arrow 88 into the position of FIG. 6, the functional element 26 is locked in that position with holding the right half of the breastbone in the raised position.

Since rack 44 and notch 48 lock together, the functional element 26 and the holding arm 24 connected to it remain in the raised position. The enormous restoring force exerted by the thorax 74 on the locking mechanism ensures that the mechanism locks solid.

The lock is released by raising the retractor 10 or the functional element 26 slightly and lifting the adjusting device 40 out of the notch 48.

To lock it again, the adjusting device 40 is swivelled back into the notch 48 (see arrow 88). This movement can be reinforced by means of spring force.

What is claimed is:

1. A retractor comprising
   a rail,
   a first holding arm protruding from said rail at an angle,
   a second holding arm extending from said rail approximately parallel to said first holding arm,
   a distance between said first and said second holding arms being adjustable,
   at least one functional element mounted on one of said two holding arms,
   said functional element having a locking section extending transversely to said holding arm and extending away from said holding arm on a side opposite to a site of a surgery,
   a swivel bracket protruding from said functional element,
   said functional element being pivotable about a pin extending roughly parallel to said holding arms via said swivel bracket,
   wherein a swiveled position of said functional element about said pin can be set by grasping it with a hand, and
   an elongated rack having a plurality of teeth along a length thereof, the rack pivotally mounted at one end to said swivel bracket, said teeth engageable with said locking section of said functional element for locking said functional element in said swiveled position.

2. The retractor of claim 1, wherein said rack, along with a locking catch, form a click mechanism.

3. The retractor of claim 2, wherein said locking catch is formed by a notch in said functional element.

4. The retractor of claim 3, wherein said locking catch is beveled on a site facing said rack.

5. The retractor of claim 1, wherein said rack points away from said retractor roughly at a right angle to a longitudinal axis of a holding arm.

6. The retractor of claim 5, wherein said rack has a T-shaped handle on an end facing away from said retractor.

7. The retractor of claim 1, wherein said functional element can be moved along said holding arm.

8. The retractor of claim 1, wherein said functional element can be removed from said holding arm.

9. The retractor of claim 1, wherein said functional element is capable of attachment to any one of said two holding arms.

10. The retractor of claim 1, wherein said functional element having at least partially a countered surface on an area where it is at an edge of a surgery site in a body.

11. The retractor of claim 10, wherein said countered surface has a crossed herring bone pattern.

12. The retractor of claim 10, wherein said countered surface structure has pyramid-shaped elevations with a rhombus-shaped base.

13. The retractor of claim 1, wherein said functional element is mounted on one of said two holding arms and a valve is mounted on the other one of said two holding arms.

\* \* \* \* \*